United States Patent
Liu (10) Patent No.: US 7,290,454 B2
(45) Date of Patent: Nov. 6, 2007

(54) PRESSURE FLOW SENSOR SYSTEMS AND PRESSURE FLOW SENSORS FOR USE THEREIN

(75) Inventor: James Z T Liu, Hudson, NH (US)

(73) Assignee: Honeywell International Inc., Morristown, NJ (US)

(*) Notice: Subject to any disclaimer, the term of this patent is extended or adjusted under 35 U.S.C. 154(b) by 152 days.

(21) Appl. No.: 11/316,036

(22) Filed: Dec. 21, 2005

(65) Prior Publication Data

US 2006/0144155 A1    Jul. 6, 2006

Related U.S. Application Data

(63) Continuation-in-part of application No. 11/002,409, filed on Dec. 2, 2004, now Pat. No. 7,059,195.

(51) Int. Cl.
*G01L 9/00* (2006.01)

(52) U.S. Cl. ........................................ 73/753

(58) Field of Classification Search ............ 73/753, 73/703, 24.06; 600/389
See application file for complete search history.

(56) References Cited

U.S. PATENT DOCUMENTS

| | | | | |
|---|---|---|---|---|
| 3,943,915 | A | * 3/1976 | Severson | 600/561 |
| 4,651,564 | A | 3/1987 | Johnson et al. | 73/204 |
| 4,660,568 | A | * 4/1987 | Cosman | 600/561 |
| 5,155,708 | A | 10/1992 | Bedi et al. | 367/152 |
| 5,675,314 | A | 10/1997 | Chaklader | 340/443 |
| 5,821,425 | A | 10/1998 | Mariani et al. | 73/703 |
| 6,055,855 | A | 5/2000 | Straub | 73/146.8 |
| 6,314,791 | B1 | 11/2001 | Rapp et al. | 73/24.06 |
| 6,517,481 | B2 | 2/2003 | Hoek et al. | 600/300 |
| 6,568,271 | B2 | 5/2003 | Shah et al. | 73/599 |

(Continued)

FOREIGN PATENT DOCUMENTS

DE       10323297 A1    12/2003

OTHER PUBLICATIONS

Takahata K et al., A wireless microsensor for monitoring flow and pressure in a blood vessel . . . , Micro Electro Mechanical Sys, IEEE, Jan. 2004, NJ, USA, pp. 216-219.

(Continued)

*Primary Examiner*—Jewel Thompson
(74) *Attorney, Agent, or Firm*—Matthew F. Lambrinos; Kermit D. Lopez; Luis M. Ortiz (57) ABSTRACT

A differential pressure flow sensor system comprises a disposable flow sensor which has upstream and downstream pressure sensing devices for detecting a differential pressure in a flow channel. Each sensing device comprises a diaphragm, a capacitor and an inductor electrically coupled to the capacitor so as to form an LC tank circuit. The capacitor and/or inductor can be mechanically coupled to the diaphragm such that a deflection of the diaphragm in response to fluid pressure applied thereto causes a change in the resonant frequency of the LC tank. The differential pressure and flow rate can be determined by detecting changes in the resonant frequency using interrogation electronics which can wirelessly interrogate the devices. A calibration capacitor and/or inductor can be formed on each sensing device and trimmed thereon for calibration purposes. Such pressure flow systems can be implemented in medical applications.

16 Claims, 5 Drawing Sheets

U.S. PATENT DOCUMENTS

| | | |
|---|---|---|
| 6,640,613 B2 | 11/2003 | Rapp et al. ................. 73/24.01 |
| 6,939,299 B1 | 9/2005 | Peterson et al. |
| 7,181,975 B1 * | 2/2007 | Bradley et al. ................ 73/724 |
| 2002/0113521 A1 | 8/2002 | Rapp et al. ............. 310/313 R |
| 2003/0076743 A1 | 4/2003 | Thompson et al. .......... 367/140 |
| 2003/0139677 A1 | 7/2003 | Fonseca et al. ............. 600/508 |
| 2003/0196477 A1 | 10/2003 | Auner et al. ............... 73/24.06 |
| 2005/0229710 A1 * | 10/2005 | O'Dowd et al. .............. 73/718 |

OTHER PUBLICATIONS

Ong K G et al., Design and application of a wireless, passive, resonant-circuit environmental . . . , Sensors & Actuators, Elsevier Sequoia, S. A. CH, vol. 93, No. 1, pp. 33-43.

* cited by examiner

PRESSURE FLOW SENSOR SYSTEMS AND PRESSURE FLOW SENSORS FOR USE THEREIN

CROSS-REFERENCE TO RELATED PATENT APPLICATION

This patent application is a Continuation-in-Part (CIP) of U.S. patent application Ser. No. 11/002,409, entitled "Disposable and Trimmable Wireless Pressure Sensor for Medical Applications," which was filed on Dec. 2, 2004 now U.S. Pat. No. 7,059,195 and is incorporated herein by reference.

TECHNICAL FIELD

Embodiments are generally related to sensors and sensing applications and, more particularly, to flow sensors and systems. Embodiments are additionally related to pressure flow sensor systems for use in medical and other applications. Additionally, embodiments are related to disposable pressure flow sensors for use in such systems and methods of manufacturing such pressure flow sensors and systems.

BACKGROUND

In single-use type applications, such as for example medical systems and instrumentation, discrete disposable sensors are required which can be implemented in a cost-effective manner. Typical flow sensors are not particularly well suited to such applications by virtue of the relatively high number of component parts, expensive materials and/or processing requirements, and high number of manufacturing-processing steps required to both produce the sensors and to integrate them into the instrumentation or apparatus of the application.

Existing discrete flow sensors utilize thermal microbridges, for example, such as those detailed in U.S. Pat. No. 4,651,564 to Johnson et al, which is assigned to Honeywell International Inc and is incorporated herein by reference. Such microbridge flow sensors include a flow sensor chip which has a thin film bridge structure thermally insulated from the chip substrate. A pair of temperature sensing resistive elements are arranged on the upper surface of the bridge either side of a heater element such that, when the bridge is immersed in the flow stream, the flow of the liquid or gas medium cools the temperature sensing element on the upstream side and promotes heat conduction from the heater element to thereby heat the temperature sensing element on the downstream side. The temperature differential between the upstream and downstream sensing elements, which increases with increasing flow speed, is converted into an output voltage by incorporating the sensing elements in a Wheatstone bridge circuit such that the flow speed of the gas or liquid can be detected by correlating the output voltage with the flow speed. When there is no fluid flow, there is no temperature differential because the upstream and downstream sensing elements are at similar temperatures.

Such thermal flow sensors suffer from a variety of drawbacks For example, the open nature of the microbridge structure can result in condensates from vapor being retained in the microbridge structure leading to uncontrolled changes in thermal response making the sensor measurements susceptible to error and instability. Additionally, the heater and sensing elements can heat the gas or liquid being measured. Furthermore, wires bonded to the heater and sensing elements retain particles suspended in the fluid and increase turbulence shifting flow response. Also, the wires are prone to damage in a high mass flux environment and during cleaning of the sensor.

Thermal flow sensors are high power consumption devices where are costly to replace and, as such, unsuitable for use as disposable flow sensors in medical and other applications. Calibration of each thermal flow sensor has to be conducted by trimming of calibration resistors which are mounted on a printed circuit board (PCB) connected to the flow sensor. Since each PCB is trimmed to calibrate a specific sensor, each sensor requires a dedicated PCB which must be disposed of when disposing of the associated flow sensor. Furthermore, manipulation of the medical apparatus by an operator is made particularly cumbersome by the fact that flow sensors and other associated devices have to be connected to the apparatus using a variety of wires and connectors.

There is a continuing need to provide improved disposable sensors which can be utilized in single use/disposable flow sensing applications more efficiently and cost effectively.

The embodiments disclosed herein therefore directly address the shortcomings of present flow sensors providing a pressure flow sensor system and a low cost disposable wireless pressure flow sensor for use therein.

BRIEF SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide for improved flow sensor systems and applications thereof.

It is another aspect of the present invention to provide for a low cost pressure flow sensor.

It is a further aspect of the present invention to provide for a low cost disposable wireless flow sensor suitable for use in medical applications, such as for example treatment apparatus.

It is an additional aspect of the present invention to provide for a method of forming a pressure flow sensor system having a low cost disposable pressure flow sensor.

The aforementioned aspects of the invention and other objectives and advantages can now be achieved as described herein. According to one aspect, a disposable flow sensor comprises one or more pressure sensing devices for detecting fluid pressure in a channel. Each pressure sensing device can comprise a diaphragm and a capacitor electrically coupled to an inductor to form an LC tank circuit. The capacitor and/or inductor can be mechanically coupled to the diaphragm such that a deflection of the diaphragm in response to fluid pressure applied thereto causes a change in the LC tank circuit inductance and/or capacitance and a change in the resonant frequency thereof. When each pressure sensing device is operatively coupled to the channel, the fluid pressure and, therefore, the flow rate of the fluid, can be determined by detecting changes in the resonant frequency using interrogation circuitry.

Employing diaphragms to detect fluid pressure to determine the fluid flow rate enables flow measurements to be conducted without heating the fluid unlike in the case of thermal microbridge sensors. Also, the pressure flow sensor exhibits a wider dynamic range than such thermal sensors.

Preferably, the resonant frequency is detectable wirelessly by means of external interrogation electronics.

The pressure sensing device can include a calibration component, such as a trimmable capacitor and/or trimmable inductor for calibrating each pressure sensing device.

Adjusting the calibration component, by trimming or otherwise, on the pressure sensing device instead of on the interrogation/signal conditioning circuit board or other associated electronics is advantageous in that the calibrated pressure sensing device including the calibration capacitor can be disposed of after use without having to dispose of associated interrogation/signal conditioning electronics.

The pressure flow sensor can therefore be implemented as a low cost and low power flow sensor which can be disposed of easily without having to replace costly electronics. The pressure flow sensor can be implemented in medical applications, such as in an intravenous drip system to measure the flow of liquid in the flow tube of the drip system. Wirelessly connecting the flow sensor to medical treatment apparatus without connecting wires or connectors enables an operator to manipulate the apparatus more easily.

According to another aspect, a differential pressure flow sensor system comprises a disposable flow sensor comprising upstream and downstream pressure sensing devices for detecting a differential pressure between upstream and downstream locations of the flow channel. Each of the pressure sensing devices comprises a diaphragm, a capacitor and an inductor electrically coupled to the capacitor so as to form an LC tank circuit. The capacitor and inductor can be mechanically coupled to the diaphragm such that a deflection of the diaphragm in response to fluid pressure applied thereto causes a change in the inductance and/or capacitance of the LC tank circuit and a change in the resonant frequency thereof. When the upstream and downstream pressure sensing devices are operatively coupled to the upstream and downstream channel locations, respectively, the differential pressure and, therefore the flow rate, can be determined by detecting changes in the resonant frequency using interrogation.

Preferably, the system includes external interrogation electronics for wirelessly detecting the change in resonant frequency of the pressure sensing devices.

The diaphragms of the pressure sensing devices can be molded in a wall of the channel at upstream and downstream locations, respectively. Advantageously, the diaphragms seal the channel sidewall so that the LC circuitry and other components of the pressure sensing devices mounted on the opposite side of the diaphragms to the fluid, and are protected from the fluid. Consequently, problems associated with fluid directly contacting the flow sensor components, such as fluid contamination and component failure are avoided.

A substrate can be coupled to the diaphragm. The inductor and/or or at least one electrode plate of the capacitor can be carried on the substrate.

The capacitor can comprise a pair of spaced apart conductive plates. One of the conductive plates can be carried on or form the diaphragm. The inductor can include a patch or layer of conductive or magnetic material coupled to the diaphragm such that deflection of the diaphragm causes a change in inductance of the inductor.

A single patch or layer of the conductive or magnetic material can be coupled to both diaphragms of the pressure sensing devices such that deflection of the diaphragms causes a change in inductance of the inductors of the pressure sensing devices.

According to yet another aspect, a method of manufacturing a flow sensor system for measuring the flow rate of fluid in a channel comprises forming a pair of disposable pressure sensing devices for measuring the pressure differential in a flow channel, and mechanically coupling the diaphragms of the pressure sensing devices to the channel at upstream and downstream locations, respectively.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

Figure 1:
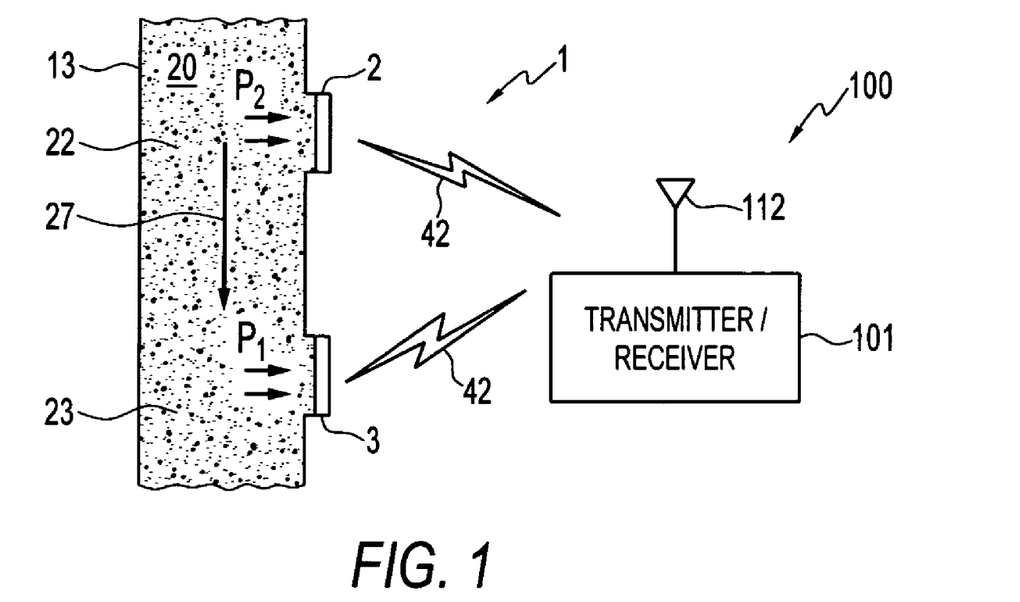
FIG. 1 illustrates a side view of a pressure flow sensor system according to a preferred embodiment.

Referring to FIG. 1 of the accompanying drawings, which illustrates a side view of a pressure flow sensor system for sensing fluid flow in a channel in accordance with an embodiment, the pressure flow sensor system 100 has a pressure flow sensor 1 which is configured as a differential pressure flow sensor which has an upstream pressure sensing device 2 and a downstream sensing device 3 for detecting the flow rate of fluid 20 flowing through a channel 13 in the direction indicated by arrow 27. Upstream pressure sensing device 2 is operatively coupled to the channel 13 at upstream location 22 for detecting fluid pressure $P_2$ whereas downstream pressure sensing device 3 is operatively coupled to channel 13 at downstream location 23 for detecting fluid pressure $P_1$. As will be explained in more detail below, pressure sensing devices 2, 3 are configured to transmit and receive data to and from a transmitter/receiver 101 which includes an antenna 112. The wireless transmission of such data is indicated in FIG. 1 by arrows 42.

In the illustrative embodiment of FIG. 1, the pressure sensing devices 2, 3 have an annular configuration; however, those skilled in the art would understand that the sensor can have different shapes and forms.

The flow rate of fluid 20 flowing in the channel 13 from the upstream location 22 to the downstream location 23 can be expressed by the following equation:

$$P_2-P_1=R_a*V+R_b*V*V \quad [1]$$

where $P_1$ and $P_2$ are the pressures at downstream and upstream locations 23, 22 respectively, V is area average flow velocity, and $R_a$ and $R_b$ are coefficients which depend on fluid properties and geometry of the tube or other channel. The flow rate V can therefore be obtained by measuring the pressure differential between upstream and downstream pressure sensing devices 2, 3.

Figure 2:
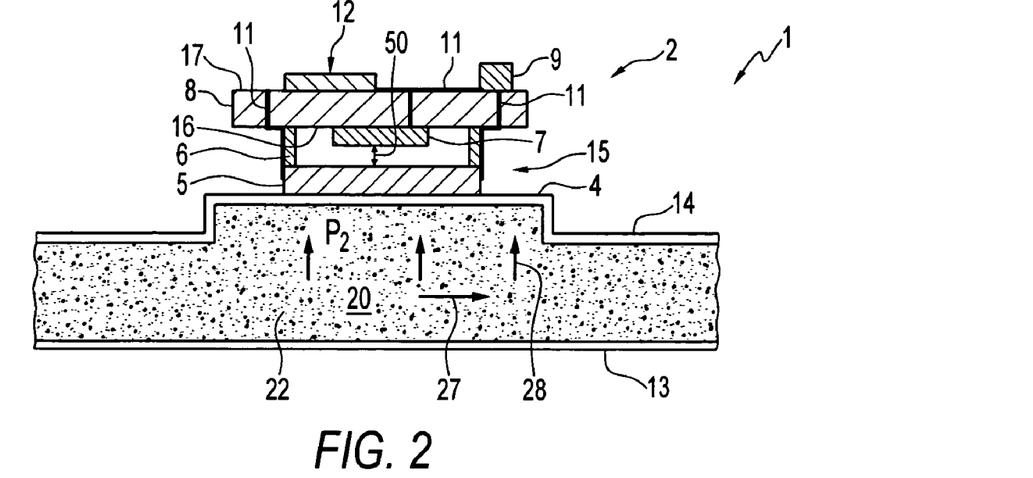
FIG. 2 illustrates an enlarged cross-sectional view of an upstream pressure sensing device of the flow sensor of FIG. 1.
Figure 3:
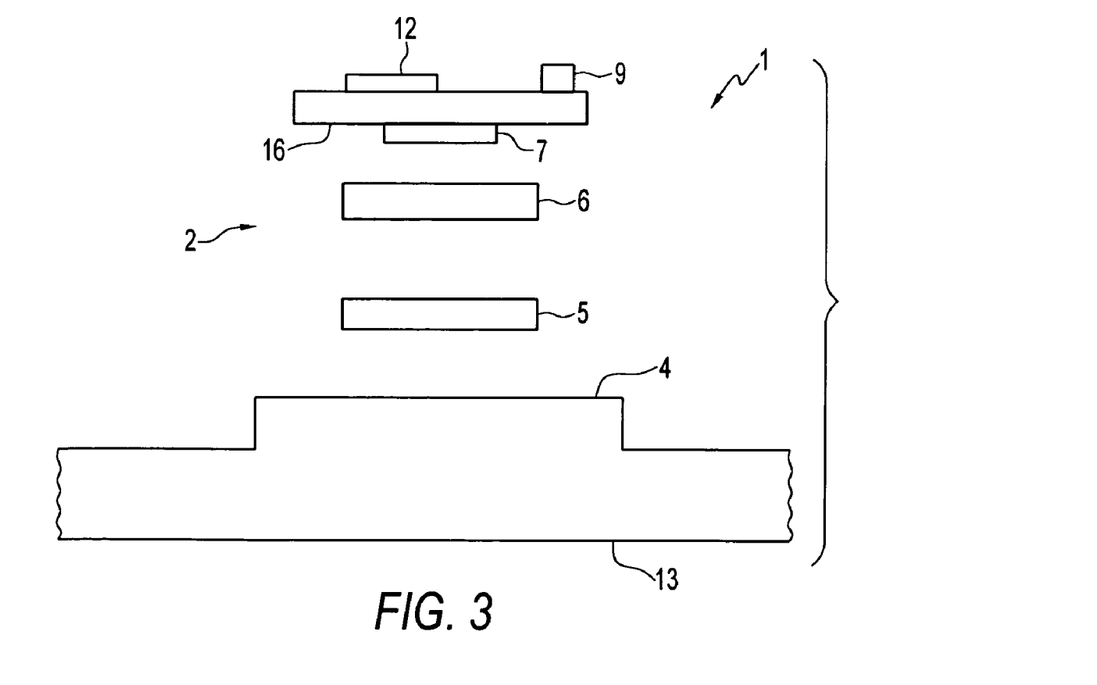
FIG. 3 illustrates a partially exploded view of the pressure sensing device shown in FIG. 2.

As best shown in FIGS. 2 & 3, which, respectively, illustrate enlarged cross-sectional and partially exploded views of the upstream pressure sensing device of FIG. 1, the upstream pressure sensing device 2 has a diaphragm 4 which is attached to the channel 13 at the upstream location 22 such that the diaphragm can deflect in response to application of fluid pressure thereon in the direction of arrows 28. In this particular embodiment, a plastic tube 13 forms the channel 13. The diaphragm 4, also made from plastic, is pre-molded into the sidewall 14 of the tube. However, the diaphragm can be mechanically coupled to the channel by other means.

Pressure sensing device 2 includes a variable capacitor 15 and inductor 12, such as planar inductor coil, electrically coupled together so as to form an LC tank circuit 12, 15. Capacitor 15 is mechanically coupled to the diaphragm 4 such that deflection of the diaphragm in response to fluid pressure applied thereto causes a change in the capacitance of the capacitor 15 and therefore a change in the resonant frequency of the LC tank circuit.

Capacitor 15 consists of a fixed electrode plate 7, attached to a rear face 16 of a substrate 8, a flexible electrode 5, attached to the outside surface of diaphragm 4 and a spacer 6, such as an 'O' ring, sandwiched between rear face 16 and flexible electrode 5 such that a predetermined air gap 50 within the spacer separates the electrodes 5, 7. Spacer 6 is arranged to support the peripheral edge of electrode 5 such that electrode plate 5 is capable of flexing towards or away from electrode plate 7, and to surround fixed electrode plate 7, which has a smaller diameter than spacer 6 and flexible electrode 5 such that the fixed electrode plate cannot electrically short with the spacer. The spacer 6 can be attached to the substrate using epoxy or other suitable adhesive.

Flexible electrode 5 can be formed by providing a conductive coating over the spacer or o-ring 6, which can be conductive or coated with a conductive material if non conductive, or by coating the outside surface of the diaphragm. Alternatively, the flexible electrode can form the diaphragm itself if there is no requirement for using a plastic diaphragm. Deflection of the diaphragm 4 causes a corresponding deflection of the electrode 5 which changes the size of the air gap 50 and, accordingly, the capacitance of the capacitor 5.

Substrate 8 can be a plastic board, PCB, polyimide film, such as a Kapton film, or any other insulating substrate. Inductor 12 can be a printed on substrate front face 17 using printing or deposition processes such as for example photolithography, etching, chemical or physical vapor deposition. A calibration capacitor 9, also surface mounted on front face 17, permits calibration of the pressure sensing device 2. Such a capacitor 9 can be soldered to the substrate and subsequently adjusted on the pressure sensing device by trimming, such as for example using a laser, or adjusted using an adjustable capacitor, to calibrate and/or offset the LC tank circuit. Alternatively, a calibration inductor can be surface mounted on the substrate and trimmed or otherwise adjusted for calibration purposes.

Figure 4:
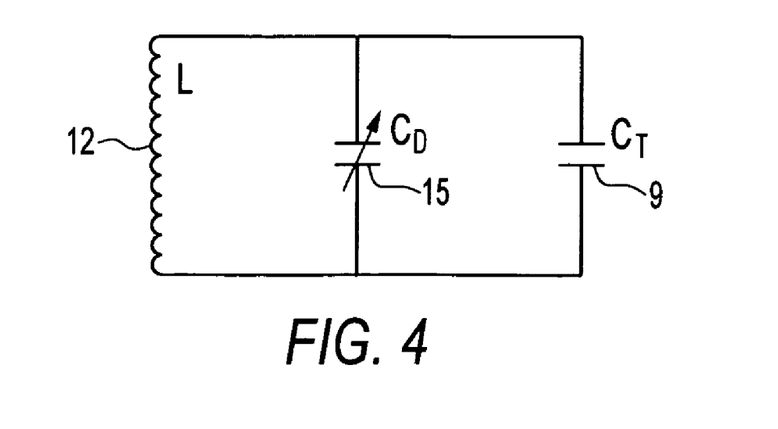
FIG. 4 illustrates an equivalent electrical circuit diagram of the pressure sensing device shown in FIG. 2.

The LC tank circuitry 15, 12 and calibration capacitor 9 are electrically interconnected by means of conductive traces or interconnects 11 formed on and in the substrate 8 and on the exterior of the spacer 6. LC circuitry including the calibration capacitor can be soldered to interconnects 11. As shown in FIG. 4, which illustrates an equivalent electrical circuit diagram representing the pressure sensing device circuitry, capacitor 15, inductor 12 and calibration capacitor 9 are electrical connected in parallel. The LC circuit 15, 12 is operatively coupled to transmitter/receiver 101 for applying an interrogation electromagnetic signal to the LC tank circuit and for receiving/conditioning the resulting LC circuit resonant signal.

Adjusting the calibration capacitor 9, by trimming or otherwise, on the pressure sensing device 2 instead of on the interrogation/signal conditioning circuit board or other associated electronics is advantageous in that the calibrated pressure sensing device 2, including the calibration capacitor, can be disposed of after use without having to dispose of associated interrogation/signal conditioning electronics.

Downstream pressure sensing device 3 of the pressure flow sensor of the illustrative embodiment of FIG. 1 is identical to upstream pressure sensing device 2 and is wirelessly connected to the transmitter/receiver 101, including the interrogation and signal conditioning electronics, in the same manner as the device 2.

The pressure flow sensor 1 is therefore a low cost sensor which can be disposed of easily without having to replace costly associated electronics. Advantageously, the diaphragms seal the channel sidewall 14 so that the LC circuitry and other components of the pressure sensing devices 2,3, mounted on the opposite side of the diaphragms to the fluid, are protected from the fluid 20. Consequently, problems associated with fluid directly contacting the flow sensor components, such as fluid contamination and component failure are avoided. Furthermore, employing diaphragms to detect fluid pressure to determine the fluid flow rate enables flow measurements to be conducting without heating the fluid unlike in the case of thermal microbridge sensors. Also, the pressure flow sensor 1 exhibits a wider dynamic range than such thermal sensors.

Pressure flow sensor 1 is also advantageous in that it provides dual functionality, that is, a pressure sensor and flow rate sensor combined.

Figure 11:
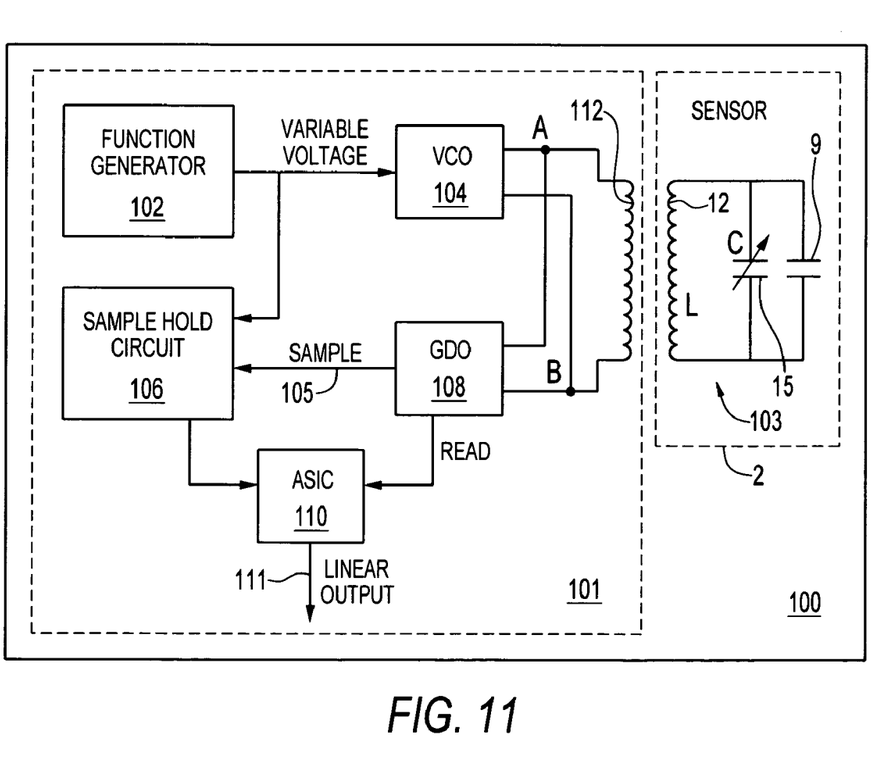
FIG. 11 illustrates an example of the electrical circuitry of the transmitter/receiver and upstream pressure sensing device of FIG. 1.

Reference will now be made to FIG. 11, which illustrates one example of the electrical circuitry of transmitter/receiver inductively coupled to the upstream pressure sensing device of FIG. 1, to explain in more detail the interrogation electronics of the flow sensor system 100. Transmitter/receiver 101 has interrogation electronics generally including a function generator 102, which provides a variable voltage to an oscillator, VCO 104, and a sample hold circuit 106. The function generator 102 can be configured as an oscillator circuit with an integrator thereof.

Output from sample hold circuit 106 can be provided to an ASIC 110. Output from VCO 104 is generally provided at node A and node B. The interrogation antenna 112 can be, for example, an inductor or coil 112, and is also generally connected to node A and node B and is located adjacent to inductor coil 12, which lies in parallel with capacitors 15, 9. Inductor coil 12 and capacitors 15, 9 together form the circuit 103 of sensing device 2. A Grid Dip Oscillator (GDO) 108 can provide sample data to sample hold circuit 106 and can additionally provide read data to ASIC 110, which in turn provides a linear output signal as indicated by arrow 111.

Two circuits 101 and 103 are therefore effectively coupled to one another through inductive coupling via the configuration of system 100. The first circuit 101 generally provides the interrogation electronic (IE) and is generally composed of function generator 102, a voltage controlled oscillator (i.e., VCO 104), sample hold circuit 106, GDO 108, ASIC 110 and an interrogation inductor or coil 112.

Inductor or coil 112 functions generally as a probe coil. Thus, when the probe coil 112 is close to the inductor coil 12 of the sensing device circuit 103, the two circuits 101 and 103 are effectively coupled through inductive coupling. As the frequency of the oscillator (VCO) 104 is swept, oscillations induced in the sensing device circuit 103 will be of very low amplitude until the test oscillator reaches the resonant frequency of the sensor tuned circuit, at which point they will "peak" or increase sharply in amplitude. A high circulating current is thus developed in the sensor circuit 103, which is reflected back into the GDO 108 as high impedance, tending to reduce the level of oscillation, or showing a "dip" in oscillation.

By measuring the "dip," the resonant frequency of the sensing device 2 and therefore the displacement (or pressure) of the variable capacitor 15 may be determined. The same interrogation circuitry 101 can be employed to interrogate the circuitry of the other pressure sensing device 3. In general, the function generator 102 oscillates at a relatively low frequency with a ramp or triangular waveform and causes VCO 104 to sweep its output between a nominal frequency range. The output of the VCO 104 is directed to probe coil 112, which is inductively coupled to the LC tank sensor circuit 103 formed by inductor or coil 12 and capacitor 15. A "dip" in the probe circuit 101 power due to a resonance condition between the LC sensor circuit 103 and the probe coil 112 can be detected by the GDO circuit 108.

A method of operating the pressure flow sensor system of FIG. 1 according to one embodiment will now be described with reference to FIGS. 1 to 4. Preparatory to normal operation of the flow sensor system 100, the calibration capacitors on the pressure sensing devices 2, 3 are trimmed so as to calibrate the LC circuit resonant signals to known pressures applied to the diaphragms of the pressure sensing devices.

Following calibration, the pressure flow sensor 1 is ready for use. Initially, channel 13 is passing fluid in the direction of arrow 27 of FIG. 1 at a certain flow rate such that the fluid at pressure sensing device 2 is applied with an associated pressure to diaphragm 4. As a result, diaphragm 4 is deflected outwards causing electrode plate 5 to flex towards electrode plate 7. The capacitance of capacitor 15 is accordingly increased in comparison to when the channel is empty and the diaphragm 4 is undeflected.

Transmitter/receiver 101 applies a wireless interrogation electromagnetic signal to the LC circuit 12, 15, causing the LC circuit to generate a resonant signal at a resonant frequency determined by the increased capacitance of capacitor 15 and the inductance of inductor 11 so that the resonant frequency represents the fluid pressure at sensing device 2. A change in upstream fluid pressure applied to diaphragm 4 of pressure sensing device 2 causes a corresponding change in deflection of the diaphragm and therefore the capacitance of the capacitor 15 which, in turn, causes a change in resonant frequency of the LC tank circuit.

Similarly, applying an interrogation electromagnetic signal to downstream pressure sensing device 3, causes the LC circuit of pressure sensing device 3 to generate a separate resonant signal with a resonant frequency representing fluid pressure at sensing device 3.

Changes in upstream and downstream fluid pressure are therefore detected as changes in resonant frequencies of the LC circuit resonant signals of the pressure sensing devices 2, 3, respectively. These resonant signals are then conditioned by associated signal conditioning circuitry (not shown) connected to the transmitter/receiver 101 so as to determine the differential pressure at upstream and downstream pressure sensing devices, and, in turn, the flow rate of the fluid using aforementioned equation 1.

Figure 5:
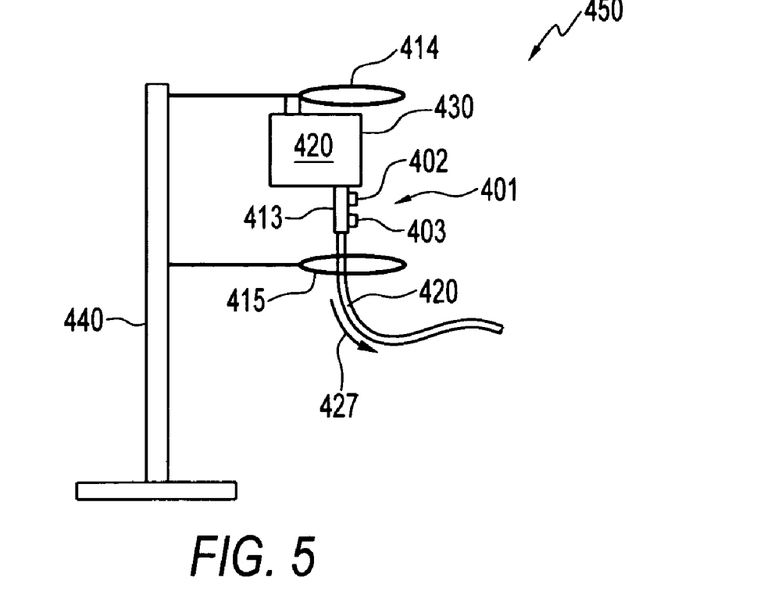
FIG. 5 illustrates a side view of a medical apparatus incorporating a pressure flow sensor according to one embodiment.

The pressure flow sensor 1 can be implemented in a variety of applications for measuring fluid flow. For example, FIG. 5 illustrates a side view of a pressure flow sensor implemented in a medical treatment system 450 according to one embodiment. Medical treatment system 450 in this particular embodiment consists of an intravenous drip system for a dialysis machine which has a self standing hanger 440, a liquid bag 430 configured to hang from hanger 440, and a flow sensor 401 incorporated in a flow tube 413 having one end communicating with the liquid bag and the other end connected to an outlet (not shown) for insertion into a patient. The flow tube 413 can be implemented as, for example a catheter, through which liquid 420 flows from the liquid bag as indicated by arrow 427. Liquid 420 can be, for example, blood. Pressure flow sensor 400 has upstream and downstream pressure sensing devices 402,403, which are identical to pressure sensing devices 2,3 of FIG. 1, and which are located proximate the end of the flow tube 413 communicating with the liquid bag.

A pair of interrogation antennas 414,415 is supported on the hanger and arranged to extend substantially around the exterior of the portion of the flow tube at which upstream and downstream pressure sensing devices 402,403 are located. The interrogation antennas 414,415, which are connected to a transmitter/receiver (not shown), serve as the transmitting and receiving coils for transmitting the interrogation electromagnetic signal and receiving the resonant signals from the pressure sensing devices 402,403.

Typically, the diameter of the inductors of the pressure sensing devices 402,403 must be at least 4 mm for a typical interrogation distance of this application. If the interrogation distance is shorter, the antennas can be clamped around the tube and sensing devices to ensure adequate inductive coupling between the interrogation circuitry and the sensing device circuitry. Preferably, each clamped interrogation antenna is configured in parallel with a respective antenna of a pressure sensing device circuit, i.e. the LC circuit of the sensing device, so as to provide the best signal/noise ratio. Antenna design could have a single antenna or, alternatively, two separated antennas. The latter configuration would be used in cases where the pressure sensing devices 2, 3 are operable in the same frequency so that the flow sensor system is easier and less costly to manufacture.

Applying the electromagnetic signals to the pressure sensing devices 402,403 and receiving the resonant signals therefrom wirelessly using the interrogation antennas 414, 415 enables the resonant frequencies of the LC circuits to be interrogated remotely to determine the pressure differential at sensing devices 402,403 and therefore the flow rate of the liquid in the flow tube. Also, the flow sensor 400 together with the flow tube 413 can be detached from the intravenous drip system and replaced with another flow sensor and tube easily without having to disconnect any electrical connectors or connections or replace any associated PCBs. Wirelessly connecting the flow sensor to the medical treatment apparatus without connecting wires or connectors enables an operator to manipulate the apparatus more easily.

The pressure sensing devices of the pressure flow sensor of the embodiments depicted in FIGS. 1-5 have variable capacitance and fixed inductance type LC tank circuits. However, as explained in more detail below, the pressure sensing devices can have variable capacitance and variable inductance type LC tank circuits or fixed capacitance and variable inductance type LC tank circuits.

Figure 6:
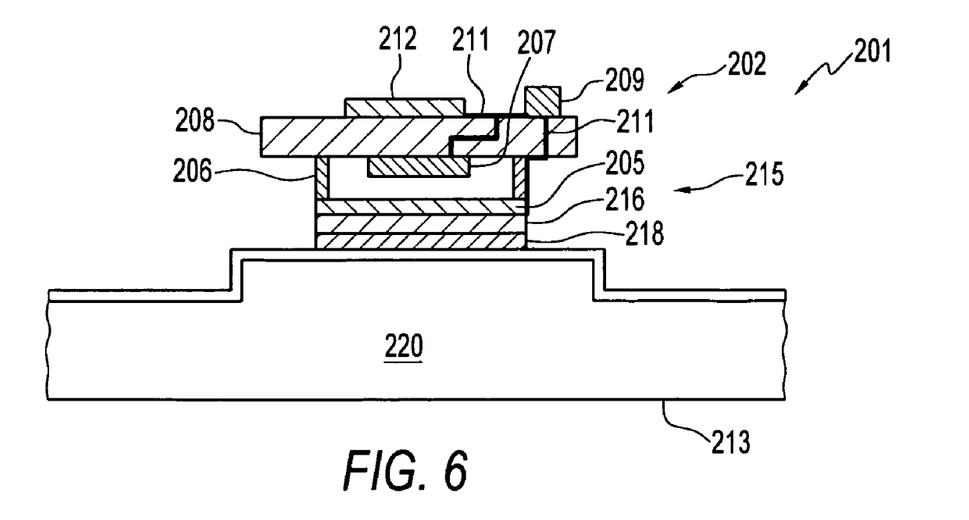
FIG. 6 illustrates an enlarged cross-sectional view of the upstream pressure sensing device of a pressure flow sensor according to another embodiment.

For example, an upstream pressure sensing device 202 having a variable capacitance and inductance type LC tank circuit used in a pressure flow sensor 201 according to another embodiment is illustrated in cross-sectional view in FIG. 6. The construction of pressure sensing device 202 and channel 213 is similar to that of pressure sensing device 2 shown in FIG. 2 save that a patch 218 is mechanically coupled to the diaphragm 204 such that deflection of the diaphragm 204 in response to fluid pressure applied thereto causes the patch 218 to change the inductance of the inductor 212 thereby changing the resonant frequency of the LC tank circuit.

Figure 7:
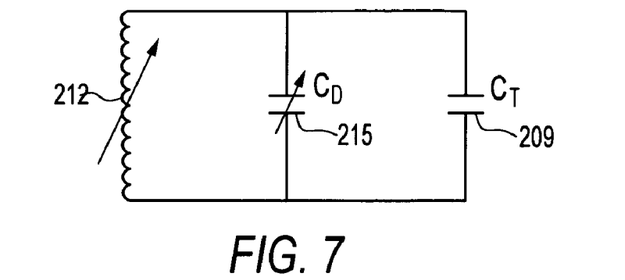
FIG. 7 illustrates an equivalent circuit diagram of the pressure sensing device of FIG. 6.

Patch 218 is bonded directly to the outside of the diaphragm 204 using adhesive and isolated from electrode plate 205 by means of an insulating layer 216 disposed between the patch 218 and electrode plate 205. Inductor 212, such as for example a planar inductor coil, and calibration capacitor 209 are both surface mounted on substrate 208 and connected to fixed and flexible electrode plates 207,205 by means of electrical interconnects 211. An equivalent electrical circuit diagram showing the resulting pressure sensing device circuitry is illustrated in FIG. 7.

Changes in fluid pressure applied to diaphragm 4 causes the patch 218 to flex further towards or away from planar inductor 212 thereby changing the inductance of inductor 212. Patch 218 can be made from conductive or magnetic material. A magnetic patch flexing towards the inductor 212 increases the inductance whereas a conductive patch flexing towards the inductor decreases the inductance. Patch 218 and isolating layer 216 are sufficiently thin to enable flexible electrode plate 205 to flex and change the capacitance of capacitor 215 in the same manner as electrode plate 5 changes the capacitance of capacitor 15 of FIG. 2. Both capacitance and inductance increase or decrease in the same direction.

The downstream pressure sensing device (not shown) of pressure flow sensor 201 is identical to upstream pressure sensing device 202. As in the case of pressure flow sensor 2 of FIG. 1, the pressure differential and fluid flow rate can be determined from the pressure flow sensor 202 using interrogation electronics (not shown) to determine and process changes in the LC tank resonant frequencies of the pressure sensing devices.

The method of operating the pressure flow sensor 201 is identical to the method of operating the pressure flow sensor 2 of the embodiment of FIG. 1 with the exception that application of pressure to diaphragm 204 changes both the capacitance and inductance of the LC tank circuit of pressure sensing device 202 and, consequently, the resonant frequency.

Figure 8:
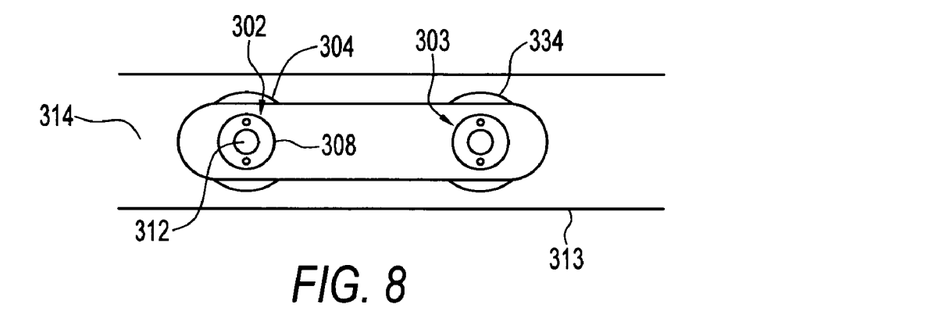
FIG. 8 illustrates a plan view taken from above a pressure flow sensor according to another embodiment.
Figure 9:
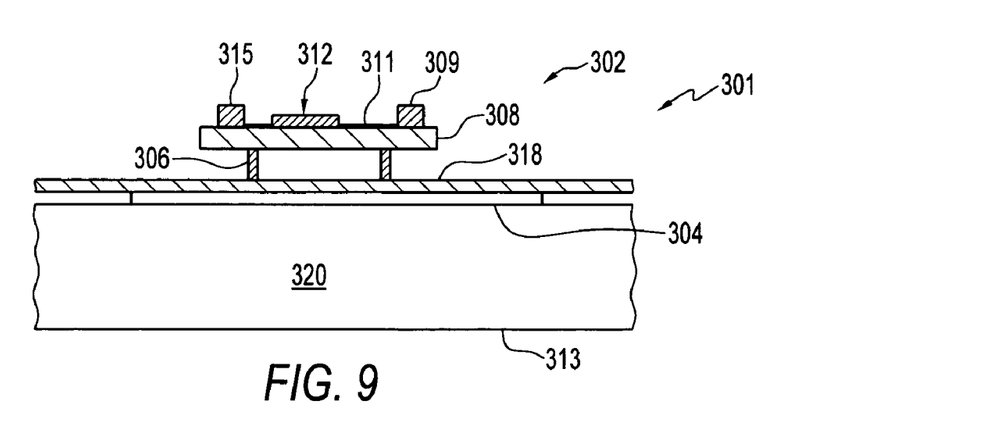
FIG. 9 illustrates an enlarged cross-sectional view of the upstream pressure sensing device of the flow sensor of FIG. 8.
Figure 10:
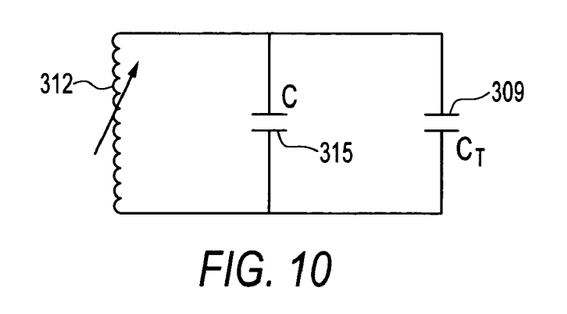
FIG. 10 illustrates an equivalent circuit diagram of the pressure sensing device of FIG. 7.

Alternatively, the pressure flow sensors can include pressure sensing devices having fixed capacitance and variable inductance type LC tank circuits for example as shown in FIG. 8 which illustrates a plan view taken from above a flow sensor 301 according to another embodiment and FIG. 9, which illustrates an enlarged cross-sectional view of an upstream pressure sensing device of the pressure flow sensor of FIG. 8. Upstream pressure sensing device 302 has premolded diaphragm 304, a patch 318 bonded to the outside surface of the diaphragm, and a substrate 308 separated from the diaphragm 304 by spacer 306 to allow patch 318 to flex towards and away from inductor 312 which is surface mounted on the substrate. Fixed capacitor 315 and calibration capacitor 309, also surface mounted on substrate 308, are electrical connected to inductor 312 by electrical interconnects 311 formed on the substrate. The pressure sensing device LC tank circuit is illustrated schematically in FIG. 10.

Changes in fluid pressure applied to diaphragm 304 causes the patch 318 to flex further towards or away from planar inductor 312 thereby changing the inductance of the inductor. As in the case of the pressure sensing device 202 of FIG. 6, the patch 318 can be made from conductive or magnetic material.

The downstream pressure sensing device 303 of pressure flow sensor 300 is identical to upstream pressure sensing device 302. As best shown in FIG. 9, patch 318 is dimensioned so that a single patch bonded to the channel wall 314 covers both diaphragm 304 of upstream pressure sensing device 302 and the diaphragm 334 of the downstream pressure sensing device 303. Using a single patch 318 instead of separate patches for each pressure sensing device simplifies manufacturing of the pressure flow sensor and further reduces cost.

As in the case of pressure flow sensor 1 of FIG. 1, the pressure differential and fluid flow rate can be determined from the pressure flow sensor 301 using interrogation electronics (not shown) to determine and process changes in the LC tank resonant frequencies of the pressure sensing devices.

The method of operating the pressure flow sensor 301 is identical to the method of operating the pressure flow sensor 1 of the embodiment of FIG. 1 with the exception that application of pressure to diaphragms 304,334 changes the inductance rather than the capacitance of the LC tank circuits of the pressure sensing devices 302,303, and, consequently, their resonant frequencies.

Flow sensors 201 and 301 according to embodiments of FIGS. 6 and 8, respectively, are low cost disposable flow sensors which also afford the same advantages as those of the pressure flow sensor 1 of FIG. 1.

The description as set forth is not intended to be exhaustive or to limit the scope of the invention. Many modifications and variations are possible in light of the above teaching without departing from the scope of the following claims.

For example, those skilled in the art would understand that each pressure flow sensor of the illustrative embodiments could have pressure sensing devices configured to have different rather than identical types of LC circuits. Furthermore, those skilled in the art would understand that a single patch could be used in conjunction with a pair of pressure sensing devices having one variable capacitance and one variable inductance type LC circuit rather than fixed capacitance and variable inductance type LC circuits as shown in FIG. 9. Additionally, those skilled in the art would understand that the flow sensors could be formed using a single pressure sensing device to measure fluid pressure indicative of flow rate instead of a pair of pressure sensing devices as shown in the illustrative embodiments.

It is contemplated that the use of the present invention can involve components having different characteristics. It is intended that the scope of the present invention be defined by the claims appended hereto, giving full cognizance to equivalents in all respects.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

Having thus described the invention what is claimed is:

1. A disposable flow sensor comprising at least one pressure sensing device for detecting fluid pressure in a channel, said at least one pressure sensing device comprising
   a diaphragm, and
   a capacitor electrically coupled to an inductor to form an LC tank circuit, said capacitor and/or inductor being mechanically coupled to said diaphragm such that a deflection of said diaphragm in response to fluid pressure applied thereto causes a change in the LC tank circuit inductance and/or capacitance and a change in the resonant frequency thereof, and wherein, when said at least one pressure sensing device is operatively coupled to said channel, said fluid pressure and said flow rate can be determined by detecting changes in said resonant frequency using interrogation.

2. A sensor as claimed in claim 1, further comprising a pair of said pressure sensing devices for detecting pressure of said fluid upstream and downstream in said channel, respectively, such that the fluid pressure differential between said upstream and downstream channel locations can be determined.

3. A sensor as claimed in claim 1, wherein said capacitor comprises a pair of spaced apart conductive plates, one of said plates being carried on or forming said diaphragm.

4. A sensor as claimed in claim 3, wherein said inductor includes a patch or layer of conductive or magnetic material carried on or forming said diaphragm such that deflection of said diaphragm causes a change in inductance of said inductor.

5. A sensor as claimed in claim 3, further comprising a substrate coupled to said diaphragm, said inductor and/or at one least one of said capacitor plates being carried on said substrate.

6. A sensor as claimed in claim 5, further comprising a calibration capacitor and/or calibration inductor carried on said substrate, said calibration capacitor and/or inductor being trimable or adjustable for calibrating said pressure sensing device.

7. A differential pressure flow sensor system comprising
   a disposable flow sensor comprising upstream and downstream pressure sensing devices for detecting a differential pressure between upstream and downstream locations of a flow channel,
   wherein each of said pressure sensing devices comprises a diaphragm, a capacitor and an inductor electrically coupled to said capacitor so as to form an LC tank circuit, said capacitor and/or inductor being mechanically coupled to said diaphragm such that a deflection of said diaphragm in response to fluid pressure applied thereto causes a change in the inductance and/or capacitance of said LC tank circuit and a change in the resonant frequency thereof and, wherein, when said upstream and downstream pressure sensing devices are operatively coupled to said upstream and downstream channel locations, respectively, said differential pressure and said flow rate can be determined by detecting changes in said resonant frequency using interrogation.

8. The system of claim 7, further comprising external interrogation electronics for wirelessly detecting said change in resonant frequency of each of said pressure sensing devices.

9. The system of claim 7, wherein said diaphragms of said pressure sensing devices are molded in a wall of said channel at upstream and downstream locations, respectively.

10. The system of claim 7, further comprising a substrate coupled to said diaphragm and, wherein said inductor and/or at least one electrode plate of said capacitor is/are carried on said substrate.

11. The system of claim 10, further comprising a calibration capacitor and/or calibration inductor formed on said substrate, said calibration capacitor and/or inductor being trimable or adjustable for calibrating said pressure sensing device.

12. The system of claim 7, wherein said capacitor comprises a pair of spaced apart conductive plates, one of said plates being carried on or forming said diaphragm.

13. The system of claim 7, wherein said inductor includes a patch or layer of conductive or magnetic material coupled to said diaphragm such that deflection of said diaphragm causes a change in inductance of said inductor.

14. The system of claim 7, wherein said inductor includes a single patch or layer of conductive or magnetic material coupled to both diaphragms of said pressure sensing devices such that deflection of said diaphragms causes a change in inductance of said inductors of said pressures sensing devices.

15. The system of claim 7, further comprising a transceiver for wireless transmitting an electromagnetic interrogation signal to said pressure sensing devices and/or for receiving resulting resonant electromagnetic signals therefrom so as to detect said changes in resonant frequency.

16. The system of claim 15, wherein said transmitter/receiver includes at least one interrogation antenna arranged so as to extend substantially around the exterior of said channel proximate said pressure sensing devices.

* * * * *